United States Patent
Wang et al.

(10) Patent No.: US 12,263,186 B2
(45) Date of Patent: Apr. 1, 2025

(54) METHODS FOR TREATING OR PREVENTING OBESITY AND BODY WEIGHT MANAGEMENT

(71) Applicant: Brillian Pharma Inc., Monmouth Junction, NJ (US)

(72) Inventors: Nuo Wang, Newtown, PA (US); Shaohui Lin, Princeton, NJ (US); Xuening Hu, Plainsboro, NJ (US)

(73) Assignee: Brillian Pharma Inc., Monmouth Junction, NJ (US)

( * ) Notice: Subject to any disclaimer, the term of this patent is extended or adjusted under 35 U.S.C. 154(b) by 767 days.

(21) Appl. No.: 17/618,030

(22) PCT Filed: Sep. 23, 2020

(86) PCT No.: PCT/US2020/052084
§ 371 (c)(1),
(2) Date: Dec. 10, 2021

(87) PCT Pub. No.: WO2021/067076
PCT Pub. Date: Apr. 8, 2021

(65) Prior Publication Data
US 2022/0257637 A1    Aug. 18, 2022

Related U.S. Application Data

(60) Provisional application No. 62/908,929, filed on Oct. 1, 2019.

(51) Int. Cl.
| | |
|---|---|
| A61K 31/732 | (2006.01) |
| A61K 9/00 | (2006.01) |
| A61K 9/08 | (2006.01) |
| A61K 31/734 | (2006.01) |
| A61K 45/06 | (2006.01) |
| A61K 47/12 | (2006.01) |

(52) U.S. Cl.
CPC .......... *A61K 31/732* (2013.01); *A61K 9/0095* (2013.01); *A61K 9/08* (2013.01); *A61K 31/734* (2013.01); *A61K 45/06* (2013.01); *A61K 47/12* (2013.01)

(58) Field of Classification Search
CPC ...... A61K 31/732; A61K 9/0095; A61K 9/08; A61K 31/734; A61K 45/06; A61K 47/12; C08J 2305/04; C08J 2305/06; C08J 3/075; A61P 3/04
See application file for complete search history.

(56) References Cited

U.S. PATENT DOCUMENTS

| | | |
|---|---|---|
| 8,754,564 B2 | 6/2014 | Bennett et al. |
| 2009/0324537 A1 | 12/2009 | Bucevschi et al. |
| 2015/0366898 A1 | 12/2015 | Heshmati et al. |
| 2016/0222134 A1 | 8/2016 | Sannino et al. |
| 2018/0289043 A1 | 10/2018 | Sannino et al. |

FOREIGN PATENT DOCUMENTS

WO    2014032676 A1    3/2014

OTHER PUBLICATIONS

Pelkman et al. Am J Clin Nutr 2007, 86, 1595-602 (Year: 2007).*
MacLean et al. Am J Physiol Regul Integr Comp Physiol, 2011, 301, R581-R600 (Year: 2011).*
Definition of prevent, Oxford English Dictionary Online, http://dictionary.oed.com/, accessed online Mar. 27, 2010, especially definition 9a. at p. 2. (Year: 2010).*
Manchanda et al. "Formulation additives used in Pharmaceutical Products: Emphasis on regulatory perspectives and GRAS" in Dosage Form Design Considerations (New York, Academic Press, 2018, pp. 773-831) (Year: 2018).*
Mirshafiey et al. "Alginate and Its Comonomer Mannuronic Acid: Medical Relevance as Drugs" in Alginates: Biology and Applications, (Berlin, Springer-Verlag, 2009, pp. 229-258). (Year: 2009).*
Skjak-Braek et al. Carbohydrate Polymers, 1989, 10, 31-54 (Year: 1989).*
Brodkorb et al. (Nature Protocols, 2019, vol. 14, pp. 991-1014) (Year: 2019).*
Woolnough et al. (International Journal of Food Science and Technology, 2008, vol. 43, pp. 2245-2256) (Year: 2008).*

* cited by examiner

*Primary Examiner* — Jonathan S Lau
*Assistant Examiner* — Sarah Grace Scrivener
(74) *Attorney, Agent, or Firm* — Fox Rothschild LLP

(57) ABSTRACT

This disclosure provides a method of administrating to a subject a two-portion solution system in a specific ingesting order to yield a water-insoluble cross-linked hydrogel mass in the stomach. The volume of the formed water-insoluble cross-linked hydrogel mass is at least 50% v/v of the total volume of the two-portion solution system. The method is useful for preventing and treating overweight and obesity.

48 Claims, No Drawings

METHODS FOR TREATING OR PREVENTING OBESITY AND BODY WEIGHT MANAGEMENT

CROSS REFERENCE TO RELATED APPLICATIONS

This application is the U.S. national phase of International Patent Application No. PCT/US20/52084, filed on Sep. 23, 2020, which claims priority under 35 U.S.C. § 119 (e) to U.S. Provisional Patent Application No. 62/908,929, filed Oct. 1, 2019. The foregoing applications are incorporated by reference herein in its entirety.

FIELD OF THE INVENTION

The present invention relates generally to methods of treating or preventing obesity and body weight management and more specifically to treating or preventing obesity and body weight management by a step-wise administration of a two-portion solution system.

BACKGROUND OF THE INVENTION

Obesity is a condition caused by increased body fat. It is a health problem of pandemic proportions. According to the World Health Organization (WHO), worldwide obesity has nearly tripled since 1975. In 2016, more than 1.9 billion adults were overweight, and of these, over 650 million were obese. In children and adolescents age group, over 340 million were overweight or obese. In the United States, the prevalence of obesity among adults was 39.8% and among youth was 18.5% in 2015-2016. Currently, there is no indication that the increase in obesity prevalence rate will reverse its trend.

Obesity has been correlated with morbidity and mortality. Obese persons with a Body mass index (BMI) of 40.0-59.9 kg/m2 have a significantly higher mortality rate than those with a BMI of 18.5-24.9 kg/m2 in life-threatening diseases of diabetes, heart diseases, respiratory disease. Because of the established health risks and substantial increases in prevalence, obesity has become a major health challenge. In many developed countries, obesity has caused increasing social and economic burden to individuals, families and the healthcare system.

There exist various strategies for treating different stages of obesities. Dietary modification and behavior modification (e.g., increased physical activity) are the most common strategies for weight loss. When obesity is mild, reduce food intake and increase physical activities can be helpful for managing body weight. These strategies aim to reduce calorie intake and increase calorie burning. Dietary modification and behavior modification work better and safer if done slowly and for long term. However, this is not always possible. Many healthy diets are vegetable, fruit, and seafood based. They are less appealing to people's tastes comparing to red meat-based, starchy, and fat-rich meals. Therefore, it is difficult for people to adhere to such healthy diet. Also, healthy diets may not be always practical for social and economic reasons. For example, meals in schools are not tailored to individual students, and there is no single best weight-loss diet for everybody.

Behavior modifications such as increasing exercise require time, self-discipline, and long term commitment. People who are overweight or obese need to get at least 150 minutes a week of moderate-intensity physical activity to prevent further weight gain or to maintain the loss of a modest amount of weight. To achieve more significant weight loss, people may need to exercise 300 minutes or more a week. However, taking time out of people's modern-day busy schedule is not always possible. Therefore, a long term regular exercise schedule is difficult to maintain. Short term vigorous exercise may produce short-lived weight-loss results, but regaining of weight is a likely outcome.

When obesity progresses to a more advanced stage, e.g., BMI is greater than 30 or BMI is 27 and greater and coupled with at least one weight-related comorbidity such as hypertension, type 2 diabetes mellitus, or dyslipidemia, prescription weight-loss medications can be added to help a person lose weight. Prescription weight-loss medications such as orlistat, lorcaserin, phentermine and topiramate, bupropion and naltrexone, and liraglutide have been approved by the FDA for obesity treatment by suppressing appetite.

Although the weight-loss prescription medications can be more effective than dietary and behavior modifications, but like all prescription medications, these prescription weight-loss medications may have unwanted adverse effects. Thus, the use of these prescription medications requires close medical supervision. Also, they may not be suitable for children, pregnant women or people who take certain medications or have chronic health conditions. The effectiveness of these medications may reduce over time and may not be suitable for long term use. Further, the regain of weight may occur when the use is stopped.

Given the prevalence of obesity, the associated health problems, and the limitations of the existing obesity treatment strategies, there exists a pressing need for methods and reagents for preventing and treating obesity and overweight.

SUMMARY OF THE INVENTION

This disclosure addresses the need mentioned above in a number of aspects. In one aspect, this disclosure provides a method for prevention or treatment of obesity or overweight. The method comprises a step-wise administration of a two-portion solution system to a subject suffering from or at risk of suffering from obesity or overweight. The two-portion solution system comprises a first solution and a second solution, and the step-wise administration comprises: (i) administrating a unit dosage of the first solution comprising a cross-linker for crosslinking a hydrogel; and (ii) administrating a unit dosage of the second solution comprising a cross-linkable hydrogel polymer after the administration of the first solution, wherein the two-portion solution system forms a cross-linked hydrogel mass that is water-insoluble and has a volume of equal to or greater than 50% (v/v) of the total volume of the two-portion solution system.

In some embodiments, the two-portion solution system can be administered no more than 2 hours prior to the subject taking a meal. In some embodiments, the two-portion solution system can be administered at least 10 minutes prior to the subject taking a meal. In some embodiments, the two-portion solution system can be administered by ingestion. In some embodiments, the second solution can be ingested within 1 minute after the ingestion of the first solution.

In some embodiments, the first solution or the second solution can be provided as a beverage. In some embodiments, the first solution or the second solution can be present in a concentrated state for use as an additive to articles of food.

In some embodiments, the cross-linker is provided for cross-linking an alginate or pectinate natural polymer. In some embodiments, the cross-linker can be a calcium salt.

Calcium salt can be any one of calcium phosphate, calcium carbonate, calcium sulfate, calcium oxide, calcium citrate, calcium lactate, calcium chloride, calcium ascorbate, calcium tartrate, calcium acetate, calcium gluconate, calcium propionate, calcium malate, and a combination thereof.

In some embodiments, the first solution has a concentration ranging from about 0.1% to about 40% (w/v) (e.g., from about 1% to about 40% (w/v), from about 1% to about 30% (w/v), from about 1% to about 25% (w/v), from about 1% to about 20% (w/v), from about 1% to about 10% (w/v), from about 2% to about 40% (w/v), from about 2% to about 30% (w/v), from about 2% to about 25% (w/v), from about 2% to about 20% (w/v), from about 2% to about 10% (w/v). In some embodiments, the first solution has a concentration ranging from about 2% to about 22% (w/v).

In some embodiments, the unit dosage of the first solution has a volume of 100 mL or below.

In some embodiments, the cross-linkable hydrogel polymer comprises one or more natural polymers, such as a polysaccharide or a salt thereof.

In some embodiments, the natural polymer can be an alginate, pectin, or pectin salt, such as an alginate or pectin monovalent salt, or partially methoxylated pectin. The monovalent salt of alginate or pectin can be any one of sodium alginate, potassium alginate, ammonium alginate, sodium pectinate, potassium pectinate, and a combination thereof.

In some embodiments, the concentration of the cross-linkable hydrogel polymer in the second solution ranges from about 0.1% to about 10% (w/v).

In some embodiments, the cross-linkable hydrogel polymer in the second solution has a viscosity of between about 3.5 cps and about 450 cps as measured in a 1% (w/v) solution.

In some embodiments, the unit dosage of the second solution has a volume of between about 100 mL and about 1000 mL.

In some embodiments, the alginate has a molecular weight of 400,000 daltons or below. The alginate may have a ratio of beta-D mannuronic acid to alpha-L guluronic acid equal to or below 1. In some embodiments, the alginate may have a ratio of beta-D mannuronic acid to alpha-L guluronic acid above 1.

In some embodiments, the pectin or pectin salt can be a partially methoxylated pectin. The partially methoxylated pectin or its salt may include a Low Methoxyl pectin, a High Methoxyl pectin or a combination thereof. In some embodiments, the partially methoxylated pectin or its salt has a molecular weight ranging between about 60,000 daltons and about 130,000 daltons.

In some embodiments, the ratio of the volume of the first solution to the volume of the second solution ranges from about 3:1 to about 1:100.

In some embodiments, the effectiveness of the two-solution system is characterized by Hydrogel Yield Ratio (HYR) determined by:

$$\text{Hydrogel Yield Ratio (HYR, \%)} = [V_d/(V \text{ Soln } 1 + V \text{ Soln } 2)] \times 100$$

where:
$V_d$ is the displacement volume of the total insoluble hydrogel matrix structure in mL,
$V_{Soln\ 1}$ is the volume of cross-linker solution in mL, and
$V_{Soln\ 2}$ is the volume of cross-linkable hydrogel polymer solution in mL In some embodiments, the first solution or the second solution further comprises an additive. The additive may include a mono- or disaccharide. In some embodiments, the additive can be one of saccharose, glucose, invert sugar, and a mixture thereof.

In some embodiments, the additive comprises an artificial sweetener. The artificial sweetener can be one of Acesulfame potassium, Aspartame, Cyclamate, Mogrosides, Saccharin, Stevia, Sucralose, Sugar alcohols, and a mixture thereof.

In some embodiments, the additive comprises a flavoring agent. The flavoring agent can be a natural flavoring agent derived from a spice, fruit or fruit juice, vegetable or vegetable juice, edible yeast, herb, bark, bud, root, leaf of similar plant material, meat, seafood, poultry, eggs, dairy products, or fermentation products thereof; or artificial flavoring agents approved by the FDA for human consumption, and a mixture thereof.

In some embodiments, the additive comprises a colorant. The colorant can be any one of the color additives approved by the FDA for use in human food and drugs.

In some embodiments, the additive comprises a pH adjusting agent. The pH adjusting agent can be any one of organic/inorganic acids or organic/inorganic bases.

In some embodiments, the additive comprises a preservative, such as benzoic acid, benzoates, parabens, sulfur dioxide, sulfites, ascorbic acid, sodium ascorbate, gallic acid, sodium gallate, butylated hydroxytoluene (BHT), butylated hydroxyanisole (BHA), and tocopherols (Vitamin E), and a mixture thereof.

In some embodiments, the additive is selected from the group consisting of a protein, a lipid, a carbohydrate, a vitamin, and a mineral component.

In some embodiments, the method further comprises administering to the subject a second agent. The second agent can be a weight-loss medication, such as orlistat, lorcaserin, phentermine and topiramate, bupropion and naltrexone, or liraglutide.

In some embodiments, the two solution system is provided as a kit and wherein the unit dosage of the first solution and the unit dosage of the second solution are provided in separate containers. The kit may further include instructions to clearly indicate the order of ingestion.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION OF THE INVENTION

This disclosure provides a method for prevention or treatment of obesity or body weight management. The method includes a step-wise administration of a two-portion solution system to a subject suffering from or at risk of suffering from obesity or overweight. The step-wise administration of a two-portion solution system, following a particular mixing order, yields a water-insoluble cross-linked hydrogel matrix structure in the stomach to occupy a portion of the stomach space.

This disclosure is based, at least in part, on unexpected discoveries that yielded gel volume was greatly affected by the sequence of mixing a calcium solution with a hydrogel solution under mild stirring. Specifically, it was found that when adding a sodium alginate solution to an acidified calcium salt solution, a larger volume of alginate-Ca gel mass was obtained when compared to the mixing in a reverse order.

It is surprising because the conventional wisdom is that the order of addition does not matter for the alginate-Ca gelation formation. Indeed, the inventors' previous studies have shown that when the two solutions are mixed with sufficient mixing/agitation applied, the yielded gel volumes are similar regardless of the order of addition. However, when the mixing/agitation is low, the yielded gel volumes can be very different, with the sodium alginate solution to calcium solution mixing process yielding a larger gel volume than when the order of addition is reversed. Extending the application of such gelling process in situ in a human subject, a gentle mixing/agitation normally happens in the stomach. The waves of stomach contraction travel toward the pylorus are propagating at a velocity averages 2.5 mm/s in a sequential manner and with 2 to 3 peristaltic contractions proceeding at any time. Each contraction takes approximately 1 min to advance from the fundus to the pylorus (Bilecen and others 2000; Kwiatek and others 2006; Schulze 2006). As a result, a sequential oral administration to a subject (e.g., human) of calcium salt and sodium alginate solutions (i.e., oral ingestion of calcium salt solution followed by oral ingestion of sodium alginate solution) will produce a larger volume of gel mass and thus generate better the satiety effect.

A. METHODS FOR PREVENTION OR TREATMENT OF OBESITY AND OVERWEIGHT

The present method features (1) a two-portion solution system comprised of a cross-linker solution (Solution 1) and a hydrogel solution containing a cross-linkable polymer (Solution 2), and (2) a procedure of administrating the two-portion solution system to a subject. The procedure includes, for example, Step 1: orally administering Solution 1 (i.e., by oral ingestion) to the subject, followed by Step 2: orally administering Solution 2 (i.e., by oral ingestion) to the subject. The two solutions are mixed in stomach to form an insoluble hydrogel matrix structure (e.g., chunks, pieces) by cross-linking induced by cross-linker. The insoluble hydrogel matrix structure chunks or pieces occupies a portion of space in the stomach and has a size large enough to prevent it from passing through the pylorus of stomach for an extended period of time until their sizes are reduced by either degradation or grinding to less than 2 mm.

The sequence of ingestion of the two solutions is of critical importance. The particular ingestion sequence of cross-linkable hydrogel polymer solution-to-cross-linking agent solution as disclosed herein yields a significantly larger volume of a water-insoluble hydrogel matrix than other ingestion sequences. The two sequentially ingested solutions are cross-linked in the stomach to form an insoluble hydrogel matrix structure that occupies a portion of space in the stomach. The hydrogel matrix structure has a size large enough to prevent it from passing through the pylorus of the stomach for an extended period of time.

Studies have shown that particle size of food emptied through the pylorus is less than 1 to 2 mm during the fed state (Thomas et al. Anaesthesia Intens Care Med 7(2):57-8 (2006); Hellström P, et al. 2006. Best Pract Res Clin Anaesthesiol 20(3):397-407 (2006)). Solids are ground to particles of a size less than 1 to 2 mm before they go through the pylorus opening.

Crosslinking is a process of forming bonds to link two polymer chains together. Both chemical cross-links and physical cross-links can be formed by proper means. Chemical cross-links are created via covalent bonds and are stable mechanically and thermally. Once formed, they are difficult to break, making the crosslinks less reversible. In contrast, physical crosslinks are created via relatively weaker bonds, such as hydrogen bonds and ionic bonds and are more reversible.

For the purpose of this disclosure, the cross-linking of the polymers by the cross-linking agent should be relatively reversible. Preferably, such cross-links can be disrupted, for example, by means of ionic bond disruption, hydrolyzation, or enzyme degradation. Thus, the preferred crosslinks in this invention are physical crosslinks. An exemplary physical crosslink type of gel is sodium alginate gel formed upon exposure to calcium ion in which ionic bonds bridge alginate chains.

Depending on the size and strength of these insoluble hydrogel chunks or pieces, they can be retained in the stomach for a longer period of time than chewed and ingested food contents. Due to delayed emptying of these insoluble hydrogel matrix chunks or pieces, they occupy certain space of the stomach for an extended period of time. Such condition triggers several possible effects for a human subject. First, it can trigger earlier onset of satiety for a subject when taken before each meal, which results in less food intake. Secondly, it maintains the satiety for an extended period of time, so the subject will go longer time between meals. Thirdly, it reduces appetite for food and snack during a day. The invention is useful for treatment and prevention of overweight, particularly for people with above the normal range of Body Mass Index (BMI).

In one aspect, this disclosure provides a method for prevention or treatment of obesity or overweight. The method comprises a step-wise administration of a two-portion solution system to a subject suffering from or at risk of suffering from obesity or overweight. The two-portion solution system comprises a first solution and a second solution, and the step-wise administration comprises: (i) administrating a unit dosage of the first solution comprising a cross-linker for crosslinking a hydrogel; and (ii) administrating a unit dosage of the second solution comprising a cross-linkable hydrogel polymer after the administration of the first solution, wherein the two-portion solution system forms a cross-linked hydrogel mass that is water-insoluble and has a volume of equal to or greater than 50% (v/v) (e.g., 60%, 70%, 80%, 8%, 90%, 100%) of the total volume of the two-portion solution system.

In some embodiments, the two-portion solution system can be administered no more than 2 hours (e.g., 1.5 hours, 1 hour, 0.5 hour) prior to the subject taking a meal. In some embodiments, the two-portion solution system can be administered at least 10 minutes (e.g., 20 minutes, 30 minutes, 40 minutes, 50 minutes, 60 minutes) prior to the subject taking a meal. In some embodiments, the two-portion solution system can be administered by ingestion. In some embodiments, the second solution (i.e., cross-linkable hydrogel polymer) can be ingested within 1 minute after the ingestion of the first solution (i.e., cross-linker).

In some embodiments, the first solution or the second solution can be provided as a beverage. In some embodiments, the first solution or the second solution can be present in a concentrated state for use as an additive to articles of food.

(a) Hydrogel Solution

The hydrogel solution contains at least one cross-linkable polymer dissolved in an aqueous medium. The cross-linkable hydrogel polymers are selected from a group of natural polymers, such as polysaccharides or their salts.

In some embodiments, the natural polymer includes a monovalent alginate salt such as sodium alginate, potassium alginate, ammonium alginate, or in combinations. Alginates are polysaccharides that provide the main structural component of brown algae (e.g., seaweeds). Alginates are linear copolymers of (1-4) linked β-d-mannuronic acid (M) and α-1-guluronic acid (G). The distribution of M and G in alginate chains gives rise to three different block types, namely blocks of poly-M, blocks of poly-G and alternating MG blocks. The chemical composition of alginate is variable according to the seaweed species, within different parts of the same plant (e.g., stem, leaf), seasonal changes and the conditions of the sea. The affinity for cations and the gel-forming properties of the alginates are mostly related to the content of G residues, as when two G residues are adjacent in the polymer they form a binding site for polyvalent cations (O. Smidsrod et al. Carbohydrates in Europe (1996), pp. 6-13).

In some embodiments, the alginate has a molecular weight of 400,000 daltons or below. The alginate may have a ratio of beta-D mannuronic acid to alpha-L guluronic acid equal to or below 1. In some embodiments, the alginate may have a ratio of beta-D mannuronic acid to alpha-L guluronic acid above 1.

Suitable low viscosity alginates can be selected from the group consisting of Manugel® GHB, Protanal® GP 1740, Protanal® LF 5/60, Protanal® LFR 5/60, Manugel® LBA, and similar pharmaceutical or non-pharmaceutical grade alginates. Suitable high viscosity alginates can be selected from the group consisting of Manugel® GMB, Protanal® GP5450, and Protanal® SF 120 RB, and similar pharmaceutical or non-pharmaceutical grade alginates.

In order to provide an aqueous diet product which does not have the fishy smell associated with conventional alginates, it is desired to use alginates overall free of smell or taste. This ensures that they can be formulated in any aqueous solution, including pure water, without any addition to its own taste. Methods for quantifying odors and taste are well known in the art and will not be disclosed in further details, however as an example, an olfactometer can be used to detect and measure odor and normally used in conjunction with human subjects in laboratory settings to quantify and qualify human olfaction.

The concentration of the cross-linkable alginate polymer solution is from about 0.1% w/v to about 40% w/v (e.g., from about 1% to about 40% (w/v), from about 1% to about 30% (w/v), from about 1% to about 25% (w/v), from about 1% to about 20% (w/v), from about 1% to about 10% (w/v), from about 2% to about 40% (w/v), from about 2% to about 30% (w/v), from about 2% to about 25% (w/v), from about 2% to about 20% (w/v), from about 2% to about 10% (w/v)). In some embodiments, the concentration of the cross-linkable hydrogel polymer in the second solution ranges from about 0.1% to about 10% (w/v).

The viscosity grades of the cross-linkable hydrogel polymers are from 3.5 cps to 450 cps (1% solution). The volume of the cross-linkable hydrogel solution can range from 100 ml to 1000 ml.

In one embodiment, the natural polymer is pectin. Pectin is a complex mixture of polysaccharides that makes up about one-third of the cell wall dry substance of higher plants (Sriamornsak, et al. Silpakorn University International Journal. 3 (1-2): 206 (2003)). The main pectin chain is composed of a (1-4) linked d-galacturonic acid residues. The polygalacturonic acid chain is partly esterified with methyl groups, and the free acid groups may be partly or fully neutralized with sodium, potassium or ammonium ions. The ratio of esterified GalA groups to total GalA groups is termed as the Degree of Esterification (DE). Depending on the DE, pectin can be separated into high methoxyl (HM) pectins and the low methoxyl (LM) pectins. HM-pectins typically have a DE ranging from 60% to 75% and those for LM-pectins ranging from 20% to 40%. These two groups of pectin gel by different mechanisms. HM-pectin gels in the presence of soluble solids such as sugar and at pH around 3.0. LM-pectins gels in the presence of certain concentration of calcium or other divalent cations. In one embodiment, the pectin polymer is an partially methoxylated LM pectin with a molecular weight ranging between about 60,000 daltons and about 130,000 daltons.

In some embodiments, the pectin salt can be sodium pectinate. The pectin salt may include a LM-pectin, a HM-pectin or a combination thereof. In some embodiments, the pectin salt comprises a pectin with a molecular weight ranging between about 60,000 daltons and about 130,000 daltons.

The concentration of the cross-linkable pectin polymer solution is from 1% w/v to 40% w/v (e.g., from about 1% to about 40% (w/v), from about 1% to about 30% (w/v), from about 1% to about 25% (w/v), from about 1% to about 20% (w/v), from about 1% to about 10% (w/v), from about 2% to about 40% (w/v), from about 2% to about 30% (w/v), from about 2% to about 25% (w/v), from about 2% to about 20% (w/v), from about 2% to about 10% (w/v)). The molecular weights of the cross-linkable pectin polymers are typically from 60,000 to 130,000 g/mol. The volume of the cross-linkable pectin polymer solution can range from 100 ml to 1000 ml.

A hydrogel solution can be prepared by dissolving at least one cross-linkable polymer in an aqueous medium. A typical procedure for producing a hydrogel solution comprises: (1) charging a proper size container with an aqueous medium; agitating the aqueous medium with a mixer; (2) under mixing, adding the cross-linkable polymer(s); and (3) continuing mixing until the content is fully dissolved or uniformly dispersed.

In some embodiments, the hydrogel solution can be prepared by: (1) first adding the cross-linkable polymer(s) into a proper size container; (2) adding a small amount of water-mixable solvents to the container to wet the cross-linkable polymer(s) to prevent the cross-linkable polymer(s) to form lumps; (3) adding an aqueous medium into the container under mixing; and (4) continuing mixing until the content is fully dissolved or uniformly dispersed. A small amount of water-mixable solvents may be added include, for example, ethyl alcohol and isopropyl alcohol. The amount used is no more than 10% of the volume of the aqueous medium.

In some embodiments, the aqueous medium is water or purified water. The aqueous medium can be used at room temperature or preheated to a temperature that is less than 60° C. to help to dissolve or disperse the cross-linkable polymers.

In order to ensure a fast and complete dispersion of the alginate in the liquid, the hydrogel solution can further comprise at least one suspending agent.

The term "suspending agent," means any agent capable of providing the desired solubility and/or dispersibility of the alginate containing composition, i.e. capable of providing an aqueous preparation which is substantially clear and without sedimentation and lumps. This is achieved when the hydrogel solution, after addition to water is either dissolved or broken down into smaller particles, is capable of passing through a 150 µm sieve. Without being bound by theory, it is believed that the suspending agent ensures that the alginate particles are diluted and separated helping to keep the alginate particles apart as they are wetted.

The ratio of the alginate to the suspending agent in the solution can be from about 0.5:1 to 10:1, more preferably from 1:1 to 2:1. The suspending agent can be selected from the group consisting of erythritol, inulin, polydextrose, dextrin, oligofructose, sucrose, succrine, Perfect Fit®, sucrose, tagatose or combinations thereof.

(b) Cross-Linker Solution

The cross-linker solution contains at least one cross-linking agent dissolves in an aqueous medium. In some embodiments, the cross-linker is provided for cross-linking alginate, pectin or pectinate natural polymer. In some embodiments, the cross-linker can be a calcium salt, such as calcium phosphate, calcium carbonate, calcium sulfate, calcium oxide, calcium citrate, calcium lactate, calcium chloride, calcium ascorbate, calcium tartrate, calcium acetate, calcium gluconate, calcium propionate, calcium malate, and a combination thereof.

In some embodiments, the first solution can be a calcium salt solution.

The crosslinker solution (e.g., calcium salt solution) has a concentration ranging from about 0.1% to about 40% on a weight by volume basis (w/v) (e.g., from about 1% to about 40% (w/v), from about 1% to about 30% (w/v), from about 1% to about 25% (w/v), from about 1% to about 20% (w/v), from about 1% to about 10% (w/v), from about 2% to about 40% (w/v), from about 2% to about 30% (w/v), from about 2% to about 25% (w/v), from about 2% to about 20% (w/v), from about 2% to about 10% (w/v)). In one embodiment, the crosslinker solution is a calcium salt solution that has a concentration ranging from 1% to 25% w/v. In yet another embodiment, the crosslinker solution is a calcium salt solution that has a concentration ranging from 2% to 22% w/v.

In some embodiments, the unit dosage of the first solution comprising a cross-linker has a volume of 100 mL or below.

A crosslinker solution can be prepared by dissolving or suspending one or more crosslinking agents that can cause the creation of crosslinking bonds among polymer chains. It is preferred that the crosslinkers are dissolved in an aqueous medium, so they are immediately available for the cross-linking process upon getting in touch of a polymer solution. The concentration of the crosslinker solution should be high enough to allow the creation of crosslinking hydrogels but not too high to provide an excess amount that is required for the polymer to gel.

A typical procedure for producing a crosslinker solution comprises: (1) charging a proper size container with an aqueous medium, agitate the aqueous medium with a mixer; (2) under mixing, adding the crosslinker(s) into the container; and (3) continuing mixing until the content is fully dissolved or uniformly dispersed.

In one embodiment, the aqueous medium is water or purified water. In another embodiment, the aqueous medium is an aqueous solution containing additional additives such as flavoring agents, taste-masking agents, viscosity adjustment agents, pH adjustment agents, antioxidants, preservatives, and colorants. In one embodiment, the water or aqueous medium can be heated to a proper temperature to promote the dissolving or dispersing of the crosslinkers. In another embodiment, the pH of the prepared crosslinker solution or suspension can be further adjusted. In yet another embodiment, additional additives can be added to the prepared crosslinker solutions or suspensions, such as flavoring agents, taste-masking agents, viscosity adjustment agents, pH adjustment agents, antioxidants, preservatives, and colorants.

(c) Step-Wise Administration

The volume ratio of the cross-linker solution to the cross-linkable polymer solution ranges from about 3:1 to about 1:100 (e.g., from about 2:1 to about 1:90, from about 2:1 to about 1:80, from about 2:1 to about 1:70, from about 2:1 to about 1:60, from about 2:1 to about 1:50, from about 2:1 to about 1:40, from about 2:1 to about 1:30, from about 2:1 to about 1:20, from about 2:1 to about 1:10, from about 2:1 to about 1:5 from about 1:1 to about 1:90, from about 1:1 to about 1:80, from about 1:1 to about 1:70, from about 1:1 to about 1:60, from about 1:1 to about 1:50, from about 1:1 to about 1:40, from about 1:1 to about 1:30, from about 1:1 to about 1:20, from about 1:1 to about 1:10, from about 1:1 to about 1:5). In some embodiments, the volume ratio of the cross-linker solution to the hydrogel solution is in the range of 1:1 to 1:10.

In some embodiments, the cross-linker solution or the cross-linkable polymer solution may further include a mono- or disaccharide sugar, such as saccharose, lactose, maltose, glucose, invert sugar, and a mixture thereof. In one embodiment, the cross-linker solution and the cross-linkable polymer solution may further include an artificial sweetener selected from the group consisting of acesulfame potassium, aspartame, cyclamate, mogrosides, saccharin, *Stevia*, sucralose, sugar alcohols, and a mixture thereof.

In some embodiments, the cross-linker solution and the cross-linkable polymer solution may further include a flavoring agent, such as spice, fruit or fruit juice, vegetable or vegetable juice, edible yeast, herb, bark, bud, root, leaf of similar plant material, meat, seafood, poultry, eggs, dairy products, or fermentation products thereof; or artificial flavoring agents that are safe for human consumption, and a mixture thereof.

In some embodiments, the cross-linker solution and the cross-linkable polymer solution may further include a colorant selected from color additives approved by the FDA for use in human food and drugs, and a mixture thereof.

In some embodiments, the cross-linker solution and the cross-linkable polymer solution may further include a pH adjusting agent, such as any organic and inorganic acids or bases. In some embodiments, the pHs of the cross-linker solution and the cross-linkable polymer solution are adjusted to between about 3.0 and about 4.0.

In some embodiments, the cross-linker solution and the cross-linkable polymer solution may further include a preservative, such as any substances or chemicals to prevent decomposition by microbial growth or by undesirable chemical changes. Examples of these preservatives include benzoic acid and benzoates, parabens, sulfur dioxide and sulfites. In some embodiments, the preservatives can be antioxidants such as ascorbic acid, sodium ascorbate, gallic acid and sodium gallate, butylated hydroxytoluene (BHT), butylated hydroxyanisole (BHA), and tocopherols (Vitamin E).

The cross-linker solution and the cross-linkable polymer solution can be pasteurized. Pasteurization is a process in which water and certain liquid foods (e.g., milk and fruit juice) are treated with mild heat, usually to less than 100° C. (or 212° F.), to eliminate pathogens and extend shelf life.

The purpose of the two-portion solution system is to produce an insoluble hydrogel matrix structure of a significant volume in the stomach of a subject, so that the insoluble hydrogel matrix structure occupies a satiety generating space in the stomach and maintains a size large enough to prevent it from passing through the pylorus of stomach for an extended period of time. Such purpose is fulfilled by a procedure, preferably before a meal, of administrating the two-portion solution system to a subject, for example, by orally administering to the subject a cross-linker solution (Solution 1) first and immediately followed by orally administering a cross-linkable polymer solution (Solution 2). When Solution 2 is ingested and gets in touch of Solution 1, an insoluble hydrogel matrix structure is formed with a sufficiently large volume that can produce satiety effect can be formed in the stomach within 15 minutes.

The water displacement volume of the insoluble hydrogel matrix structure produced in the stomach by this method can be estimated by a simulation experiment comprising steps of: (1) charging 40 ml simulated gastric fluid (e.g., 0.1 N hydrochloric acid solution) into a suitably sized beaker equipped with a magnetic mixing bar rotating at 150 rpm; (2) adding the cross-linker solution into the beaker and mixing for at least 15 seconds; (3) adding the cross-linkable polymer solution into the beaker and continuing mixing for 15 minutes; (4) pouring the entire content onto a stainless steel screen (20-40 mesh) to collect the insoluble hydrogel matrix structure mass and drain all free water; (5) preparing a volumetric cylinder containing a fixed volume of water ($V_0$), add the collected gel mass into the cylinder and record the volume ($V_t$); and (6) calculating the displacement volume of the insoluble hydrogel matrix structure ($V_d$) using equation:

$$V_d = V_t - V_0 \qquad \text{Equation 1}$$

Using the calculated Vd, a Hydrogel Yield Ratio (HYR, %) can be calculated by the following equation:

$$\text{Hydrogel Yield Ratio (HYR, \%)} = [V_d/(V_{Soln\ 1} + V_{Soln\ 2})] \times 100 \qquad \text{Equation 2}$$

Where:
$V_d$ is the displacement volume of the total insoluble hydrogel matrix structure in mL
$V_{Soln\ 1}$ is the volume of cross-linker solution in mL
$V_{Soln\ 2}$ is the volume of cross-linkable polymer solution in mL The HYR measures the capability of how large of a volume that the method of using the two-portion solution system in this disclosure is capable of producing and can be used for comparing the capacity with other prior art methods. The HYR produced by the method disclosed in this invention should be consistently above 50%.

The total volume of the insoluble hydrogel matrix structure mass can be made up by the volume of one hydrogel chunk which is at least 20 mm in length in any dimensions. The total volume of the insoluble hydrogel matrix structure mass can also be made up by the volumes of many smaller insoluble hydrogel matrix chunks or pieces. In such case, 95% of the smaller insoluble hydrogel chunks or pieces are at least 4 mm in length in any dimensions.

B. COMPOSITIONS AND KITS

This disclosure also provides composition (e.g., pharmaceutical compositions) comprising the first solution comprising a cross-linker or the second solution comprising a cross-linkable polymer.

Compositions for use in accordance with the present methods may be formulated in a conventional manner using one or more physiologically acceptable carriers or excipients. For oral administration, the pharmaceutical compositions may take the form of, for example, tablets, prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. The tablets are then constituted to a solution or suspension at the time of administration. Liquid preparations for oral administration may take the form of, for example, solutions, syrups or suspensions, or they may be presented as a dry product for constitution with water or other suitable vehicles before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Compositions that may oxidize and lose activity, especially in a liquid or semisolid form, may be prepared in a nitrogen atmosphere or sealed in a type of package that excludes oxygen from headspace.

Other active agents may also be included in formulations, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

A composition described herein can be provided in a kit. In one embodiment, the kit includes (a) a container that contains the composition, and optionally (b) informational material. The informational material can be descriptive, instructional, marketing or other material that relates to the methods described herein and/or the use of the agents for therapeutic benefit. In an embodiment, the kit also includes an additional therapeutic agent. For example, the kit includes a first container that contains the composition and a second container for the additional therapeutic agent.

The informational material of the kits is not limited in its form. In one embodiment, the informational material can include information about production of the composition, concentration, date of expiration, batch or production site information, and so forth. In one embodiment, the informational material relates to methods of administering the composition, e.g., in a suitable dose, dosage form, or mode of administration (e.g., a dose, dosage form, or mode of administration described herein), to treat a subject in need thereof. In one embodiment, the instructions provide a dosing regimen, dosing schedule, and/or route of administration of the composition or the additional therapeutic agent. The information can be provided in a variety of formats, including printed text, computer-readable material, video recording, or audio recording, or information that contains a link or address to substantive material.

In addition to the composition, the kit can include other ingredients, such as a solvent or buffer, a stabilizer, or a preservative. The composition can be provided in any form, e.g., liquid, dried or lyophilized form. When the agents are provided in a liquid solution, the liquid solution preferably is an aqueous solution. When the agents are provided as a dried form, reconstitution generally is by the addition of a suitable solvent and acidulant. The acidulant and solvent, e.g., an aprotic solvent, sterile water, or a buffer, can optionally be provided in the kit.

The kit can include one or more containers for the composition or compositions containing the first solution or the second solution. In some embodiments, the kit contains separate containers, dividers or compartments for the composition and informational material. For example, the composition can be contained in a bottle or vial, and the informational material can be contained in a plastic sleeve or packet. In other embodiments, the separate elements of the kit are contained within a single, undivided container. For example, the composition is contained in a bottle or vial that has attached thereto the informational material in the form of a label. In some embodiments, the kit includes a plurality (e.g., a pack) of individual containers, each containing one or more unit dosage forms (e.g., a dosage form described herein) of the agents.

The kit optionally includes a device suitable for administration of the composition or other suitable delivery device. The device can be provided pre-loaded with one or both of the agents or can be empty, but suitable for loading.

In some embodiments, the two solution system is provided as a kit and wherein the unit dosage of the first solution and the unit dosage of the second solution are provided in separate containers. The kit may further include instructions to clearly indicate the order of ingestion.

C. DEFINITIONS

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The term "solubility" means the property of the composition to dissolve and/or disperse in a liquid solvent to form a homogeneous solution of the hydrogel (e.g., alginate). As an example can be mentioned that said solubility is achieved when the composition according to the invention after addition to liquid is either dissolved or broken down into smaller particles capable of passing through a 150 μm sieve.

The terms "decrease," "reduced," "reduction," "decrease," or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent," which is a biologically, physiologically, or pharmacologically active substance (or substances) that acts locally or systemically in a subject.

The terms "therapeutic agent," "therapeutic capable agent," or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, the term "pharmaceutical grade" means that certain specified biologically active and/or inactive components in the drug must be within certain specified absolute and/or relative concentration, purity and/or toxicity limits and/or that the components must exhibit certain activity levels, as measured by a given bioactivity assay. Further, a "pharmaceutical grade compound" includes any active or inactive drug, biologic or reagent, for which a chemical purity standard has been established by a recognized national or regional pharmacopeia (e.g., the U.S. Pharmacopeia (USP), British Pharmacopeia (BP), National Formulary (NF), European Pharmacopoeia (EP), Japanese Pharmacopeia (JP), etc.). Pharmaceutical grade further incorporates suitability for administration by means including topical, ocular, parenteral, nasal, pulmonary tract, mucosal, vaginal, rectal, intravenous, and the like.

"Combination" therapy, as used herein, unless otherwise clear from the context, is meant to encompass administration of two or more therapeutic agents in a coordinated fashion, and includes, but is not limited to, concurrent dosing. Specifically, combination therapy encompasses both co-administration (e.g., administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. See, e.g., Kohrt et al. (2011) Blood 117:2423.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

D. EXAMPLES

Example 1: Demonstration of the Effect of Solution Addition Order of the Two-Portion Solution System (Sodium Alginate & Calcium Solutions) on the Hydrogel Yield Ratio (HYR, %)

Preparation of Cross-Linker Solution (Solution 1)

Weigh 22.14 g Calcium Acetate and 18.24 g Calcium Lactate. In a 200 ml volumetric flask, add 180 ml purified water. Add the weighted Calcium Acetate and Calcium Lactate into the flask, mix until fully dissolved. Qs volume to 200 nil.

Preparation of Cross-Linkable Polymer Solution (Solution 2).

Weight 15.2 g of Sodium Alginate (Protanal CR8223). In a 3000 mL container, charge 2100 ml purified water. Use a mechanical mixer, create a vortex. Add the weighed Sodium Alginate into the vortex. Continue mixing until a clear light brown solution is obtained.

Alginate-Ca Gelling Study Example: Solution Addition Order: Add Solution 2 First, Followed by the Addition of Solution 1

In a 600 ml beaker, add 40 ml 0.1 N HCl solution and stirred with a magnetic bar at 150 rpm. Under stirring, add 290 ml of Solution 2. Mix the content for 120 seconds at 150 rpm, followed by adding 25 ml of Solution 1. Continue mixing for 15 minutes.

Pour the content of the container onto a 30 mesh screen. The insoluble hydrogel matrix structure is collected on the screen. The displacement volume $V_d$ is measured by using a 2000 ml volumetric cylinder filled with 400 ml of water ($V_o$). The screened insoluble hydrogel matrix structure is added into the volumetric cylinder and the increased volume is recorded ($V_t$). The $V_d$ is calculated by Equation 1. The Hydrogel Yield Ratio (HYR, %) is calculated using the obtained $V_d$ using Equation 2. Repeat the experiment in triplicates. The results are provided in table below.

| Sample ID | 8069-17A | 8069-17B | 8069-17C |
|---|---|---|---|
| Volume of 0.1N HCl Solution, mL | 40 | 40 | 40 |
| Volume of Solution 1 ($V_{Soln\ 1}$), mL | 25 | 25 | 25 |
| Volume of Solution 2 ($V_{Soln\ 2}$), mL | 290 | 290 | 290 |
| ($V_{Soln\ 1} + V_{Soln\ 2}$), mL | 315 | 315 | 315 |

-continued

| Sample ID | 8069-17A | 8069-17B | 8069-17C |
|---|---|---|---|
| Sequence of Solution Addition | Solution 2 followed by Solution 1 | Solution 2 followed by Solution 1 | Solution 2 followed by Solution 1 |
| $V_d$, mL | 115 | 119 | 101 |
| Hydrogel Yield Ratio (HYR), % | 37 | 38 | 32 |

Alginate-Ca Gelling Example: Solution Addition Order: Solution 1 First, Followed by solution 2

In a 600 ml beaker, add 40 ml 0.1 N HCl solution and stirred with a magnetic bar at 150 rpm. Under stirring, add 25 ml of Solution 1. Mix the content for 120 seconds at 150 rpm, followed by adding 290 ml of Solution 2. Continue mixing for 15 minutes.

Pour the content of the container onto a 30 mesh screen. The insoluble hydrogel matrix structure is collected on the screen. The displacement volume $V_d$ is measured by using a 2000 ml volumetric cylinder filled with 400 ml of water ($V_0$). The screened insoluble hydrogel matrix structure is added into the volumetric cylinder and the increased volume is recorded ($V_{in}$). The $V_d$ is calculated by subtracting $V_0$ from $V_{in}$. The Hydrogel Yield Ratio (HYR, %) is calculated using the obtained $V_d$ using Equation 1. Repeat the experiment in triplicates.

| Sample ID | 8069-17D | 8069-17E | 8069-17F |
|---|---|---|---|
| Volume of 0.1N HCl Solution, mL | 40 | 40 | 40 |
| Volume of Solution 1 ($V_{Soln\ 1}$), mL | 25 | 25 | 25 |
| Volume of Solution 2 ($V_{Soln\ 2}$), mL | 290 | 290 | 290 |
| ($V_{Soln\ 1} + V_{Soln\ 2}$), mL | 315 | 315 | 315 |
| Sequence of Solution Addition | Solution 1 followed by Solution 2 | Solution 1 followed by Solution 2 | Solution 1 followed by Solution 2 |
| $V_d$, mL | 210 | 220 | 230 |
| Hydrogel Yield Ratio (HYR), % | 67 | 70 | 73 |

The HYR % of gel mass produced by solution addition order of Solution 1 followed by Solution 2 is much higher than that produced by solution addition order of Solution 2 followed by Solution 1.

Example 2: Effect of Pasteurization on Alginate-Ca Gelling HYR %

Preparation of Cross-Linker Solution (Solution 1)

Weigh 27.67 g Calcium Acetate and 22.80 g Calcium Lactate. In a container, add 250 ml purified water. Add the weighted Calcium Lactate and Calcium Acetate into the container under stirring, continue mixing until fully dissolved. Place the prepared solution on a hot plate and heat to the boiling point, and maintain the solution at boiling point for 180 seconds.

Preparation of Cross-Linkable Polymer Solution (Solution 2).

Weight 7.243 g of Sodium Alginate (Protanal CR8223). In a glass container, charge 1000 ml purified water. Use a mechanical mixer, create a vortex. Add the weighed Sodium Alginate into the vortex. Continue mixing until a clear light brown solution is obtained. Place the prepared solution on a hot plate and heat to the boiling point, and maintain the solution at boiling point for 180 seconds.

Alginate-Ca Gelling Example: Solution Addition Order: Add Solution 1 First, Followed by Solution 2

In a 600 ml beaker, add 40 ml 0.1 N HCl solution and stirred with a magnetic bar at 150 rpm. Under stirring, add 290 ml of Solution 2. Mix the content for 120 seconds at 150 rpm, followed by adding 25 ml of Solution 1. Continue mixing for 15 minutes.

Pour the content of the container onto a 30 mesh screen. The insoluble hydrogel matrix structure is collected on the screen. The displacement volume $V_d$ is measured by using a 2000 ml volumetric cylinder filled with 400 ml of water ($V_0$). The screened insoluble hydrogel matrix structure is added into the volumetric cylinder and the increased volume is recorded ($V_{in}$). The $V_d$ is calculated by subtracting $V_0$ from $V_{in}$. The Hydrogel Yield Ratio (HYR, %) is calculated using the obtained $V_d$ using Equation 1. Repeat the experiment in triplicates.

| Sample ID | WNIP-117 |
|---|---|
| Volume of 0.1N HCl Solution, mL | 40 |
| Volume of Solution 1 ($V_{Soln\ 1}$), mL | 25 |
| Volume of Solution 2 ($V_{Soln\ 2}$), mL | 290 |
| ($V_{Soln\ 1} + V_{Soln\ 2}$), mL | 315 |
| Sequence of Solution Addition | Solution 1 followed by Solution 2 |
| $V_d$, mL | 200 |
| Hydrogel Yield Ratio (HYR), % | 63 |

This example demonstrated that pasteurizing the two solutions does not negatively affect the HYR %. The HYR % of the produced gel mass is more than 50%.

Example 3: Demonstrating the Effect of Lower Concentration but Higher Volume of Cross-Linker Solution on HYR %

Preparation of Cross-Linker Solution (Solution 1)

Weigh 3.967 g Calcium Acetate and 5.469 g Calcium Lactate. In a 200 ml volumetric flask, add 180 ml purified water. Add the weighted Calcium Acetate and Calcium Lactate into the flask, mix until fully dissolved. Qs volume to 200 nil.

Preparation of Cross-Linkable Polymer Solution (Solution 2)

This solution is prepared following the same procedure for Solution 2 from example 1.

Alginate-Ca Gelling Study: Solution Addition Order: Add Solution 1 First, Followed by Solution 2

In a 600 ml beaker, add 40 ml 0.1 N HCl solution and stirred with a magnetic bar at 150 rpm. Under stirring, add 60 ml of Solution 1. Mix the content for 120 seconds at 150 rpm, followed by adding 240 ml of Solution 2. Continue mixing for 15 minutes.

Pour the content of the container onto a 30 mesh screen. The insoluble hydrogel matrix structure is collected on the screen. The displacement volume $V_d$ is measured by using a 1000 ml volumetric cylinder filled with 300 ml of water ($V_0$). The screened insoluble hydrogel matrix structure is added into the volumetric cylinder and the increased volume is recorded ($V_t$). The $V_d$ is calculated by Equation 1. The Hydrogel Yield Ratio (HYR, %) is calculated using the obtained $V_d$ using Equation 2. Repeat the experiment in triplicates. The results are provided in the table below.

| Sample ID | WNIP-103 |
|---|---|
| Volume of 0.1N HCl Solution, mL | 40 |
| Volume of Solution 1 ($V_{Soln\ 1}$), mL | 60 |
| Volume of Solution 2 ($V_{Soln\ 2}$), mL | 240 |
| ($V_{Soln\ 1} + V_{Soln\ 2}$), mL | 300 |
| Sequence of Solution Addition | Solution 1 followed by Solution 2 |
| $V_d$, mL | 170 |
| Hydrogel Yield Ratio (HYR), % | 57 |

The result shows that a >50% HYR is obtained.

Example 4: Calcium Propionate & Calcium Gluconate Combination at 20.92% Concentration as Cross-Linking Agents Preparation of Cross-Linker Solution (Solution 1)

Weigh 84.6 g Calcium Propionate and 20 g Calcium Gluconate. In a container, add 450 ml purified water. Add the weighted Calcium Propionate and Calcium Gluconate into the container under stirring, heat the mixture to 60° C., continue mixing until fully dissolved. Raise the temperature to 100° C. for 3 minutes. Cool the solution to room temperature. Qs volume to 500 nil.

Preparation of Cross-Linkable Polymer Solution (Solution 2)

Weight 21.72 g of Sodium Alginate (PH124, JRS VivaPharma). In a proper container, charge 3000 ml purified water. Use a mechanical mixer, create a vortex. Add the weighed Sodium Alginate into the vortex. Continue mixing until a clear light brown solution is obtained. Place the prepared solution on a hot plate and heat to the boiling point, and maintain the solution at boiling point for 3 minutes.

Alginate-Ca Gelling Study: Solution Addition Order: Add Solution 1 First, Followed by Solution 2

In a 600 ml beaker, add 40 ml 0.1 N HCl solution and stirred with a magnetic bar at 150 rpm. Under stirring, add 25 ml of Solution 1. Mix the content for 120 seconds at 150 rpm, followed by adding 290 ml of Solution 2. Continue mixing for 15 minutes.

Pour the content of the container onto a stainless steel 30 mesh screen. The insoluble hydrogel matrix structure is collected on the screen. The displacement volume $V_d$ is measured by using a 2000 ml volumetric cylinder filled with 400 ml of water ($V_0$). The screened insoluble hydrogel matrix structure is added into the volumetric cylinder and the increased volume is recorded ($V_t$). The $V_d$ is calculated by Equation 1. The Hydrogel Yield Ratio (HYR, %) is calculated using the obtained $V_d$ using Equation 2. Repeat the experiment in triplicates. The results are provided in table below.

| Sample ID | 8069-23 |
|---|---|
| Volume of 0.1N HCl Solution, mL | 40 |
| Volume of Solution 1 ($V_{Soln\ 1}$), mL | 25 |
| Volume of Solution 2 ($V_{Soln\ 2}$), mL | 290 |
| ($V_{Soln\ 1} + V_{Soln\ 2}$), mL | 315 |
| Sequence of Solution Addition | Solution 1 followed by Solution 2 |
| $V_d$, mL | 180 |
| Hydrogel Yield Ratio (HYR), % | 57 |

The HYR % of the produced gel mass is more than 50%.

Example 5: Calcium Chloride ($CaCl_2$) as a Cross-Linking Agent in the Presence of Citric Acid Preparation of Cross-Linker Solution (Solution 1)

Weigh 55.5 g Calcium Chloride and 26 g Citric Acid anhydrous. In a container, add 450 ml purified water. Add the weighted Calcium Chloride and Citric Acid into the container under stirring, continue mixing until fully dissolved. Raise the temperature to 90° C. for 30 seconds. Cool the solution to room temperature. Qs volume to 500 nil.

Preparation of Cross-Linkable Polymer Solution (Solution 2)

This solution is prepared in example 4.

Alginate-Ca Gelling Study: Solution Addition Order: Add Solution 1 First, Followed by Solution 2

In a 600 ml beaker, add 40 ml 0.1 N HCl solution and stirred with a magnetic bar at 150 rpm. Under stirring, add 25 ml of Solution 1. Mix the content for 120 seconds at 150 rpm, followed by adding 290 ml of Solution 2. Continue mixing for 15 minutes.

Pour the content of the container onto a stainless steel 30 mesh screen. The insoluble hydrogel matrix structure is collected on the screen. The displacement volume $V_d$ is measured by using a 2000 ml volumetric cylinder filled with 400 ml of water ($V_0$). The screened insoluble hydrogel matrix structure is added into the volumetric cylinder and the increased volume is recorded ($V_t$). The $V_d$ is calculated by Equation 1. The Hydrogel Yield Ratio (HYR, %) is calculated using the obtained $V_d$ using Equation 2. Repeat the experiment in triplicates. The results are provided in the table below.

| Sample ID* | 8069-26B |
|---|---|
| Volume of 0.1N HCl Solution, mL | 40 |
| Volume of Solution 1 ($V_{Soln\ 1}$), mL | 25 |
| Volume of Solution 2 ($V_{Soln\ 2}$), mL | 290 |
| ($V_{Soln\ 1} + V_{Soln\ 2}$), mL | 315 |
| Sequence of Solution Addition | Solution 1 followed by Solution 2 |
| $V_d$, mL | 210 |
| Hydrogel Yield Ratio (HYR), % | 67 |

The HYR % of the produced gel mass is more than 50%.

Example 6: Calcium Ascorbate as a Cross-Linking Agent

Preparation of Cross-Linker Solution (Solution 1)

Weigh 35.35 g Calcium Ascorbate. In a container, add 200 ml purified water. Add the weighted Calcium Ascorbate into the container under stirring, continue mixing until fully dissolved.

Preparation of Cross-Linkable Polymer Solution (Solution 2)

Weight 4.2 g of Sodium Alginate (Protanal CR8223). In a proper container, charge 600 ml purified water. Use a mechanical mixer, create a vortex. Add the weighed Sodium Alginate into the vortex. Continue mixing until a clear light brown solution is obtained.

Alginate-Ca Gelling Study: Solution Addition Order: Add Solution 1 First, Followed by Solution 2

In a 600 ml beaker, add 40 ml 0.1 N HCl solution and stirred with a magnetic bar at 150 rpm. Under stirring, add 60 ml of Solution 1. Mix the content for 120 seconds at 150 rpm, followed by adding 300 ml of Solution 2. Continue mixing for 15 minutes.

Pour the content of the container onto a stainless steel 30 mesh screen. The insoluble hydrogel matrix structure is collected on the screen. The displacement volume $V_d$ is measured by using a 1000 ml volumetric cylinder filled with 300 ml of water ($V_0$). The screened insoluble hydrogel matrix structure is added into the volumetric cylinder and the increased volume is recorded ($V_t$). The $V_d$ is calculated by Equation 1. The Hydrogel Yield Ratio (HYR, %) is calculated using the obtained $V_d$ using Equation 2. Repeat the experiment in triplicates. The results are provided in table below.

| Sample ID* | WNIP-93 |
| --- | --- |
| Volume of 0.1N HCl Solution, mL | 40 |
| Volume of Solution 1 ($V_{Soln\ 1}$), mL | 60 |
| Volume of Solution 2 ($V_{Soln\ 2}$), mL | 300 |
| ($V_{Soln\ 1} + V_{Soln\ 2}$), mL | 360 |
| Sequence of Solution Addition | Solution 1 followed by Solution 2 |
| $V_d$, mL | 210 |
| Hydrogel Yield Ratio (HYR), % | 58 |

The HYR % of the produced gel mass is more than 50%.

Example 7: Demonstration of the Effect of Solution Addition Order of the Two-Portion Solution System (Pectin & Calcium Solutions) on the Hydrogel Yield Ratio (HYR, %)

Preparation of Cross-Linker Solution (Solution 1)

A 11.1% w/v calcium solution is prepared by fully dissolving Calcium Chloride in purified water.

Preparation of Cross-Linkable Polymer Solution (Solution 2).

Weight 13.03 g of Low Methoxy Pectin. In a proper size container, charge 600 ml purified water. Use a mechanical mixer, create a vortex. Add the weighed LM Pectin into the vortex. Continue mixing until a clear solution is obtained.

Pectin-Ca Gelling Study Example: Solution Addition Order: Add Solution 2 First, Followed by Solution 1

In a 600 ml beaker, add 40 ml 0.1 N HCl solution and stirred with a magnetic bar at 150 rpm. Under stirring, add 290 ml of Solution 2. Mix the content for 120 seconds at 150 rpm, followed by adding 25 ml of Solution 1. Continue mixing for 15 minutes.

Pour the content of the container onto a 30 mesh screen. The insoluble hydrogel matrix structure is collected on the screen. The displacement volume $V_d$ is measured by using a 2000 ml volumetric cylinder filled with 400 ml of water ($V_0$). The screened insoluble hydrogel matrix structure is added into the volumetric cylinder and the increased volume is recorded ($V_t$). The $V_d$ is calculated by Equation 1. The Hydrogel Yield Ratio (HYR, %) is calculated using the obtained $V_d$ using Equation 2. Repeat the experiment in triplicates. The results are provided in table below.

| Sample ID | 8069-40A |
| --- | --- |
| Volume of 0.1N HCl Solution, mL | 40 |
| Volume of Solution 1 ($V_{Soln\ 1}$), mL | 25 |
| Volume of Solution 2 ($V_{Soln\ 2}$), mL | 290 |
| ($V_{Soln\ 1} + V_{Soln\ 2}$), mL | 315 |
| Sequence of Solution Addition | Solution 2 followed by Solution 1 |
| $V_d$, mL | 60 |
| Hydrogel Yield Ratio (HYR), % | 19.1 |

Pectin-Ca Gelling Example: Solution Addition Order: Solution 1 First, Followed by Solution 2

In a 600 ml beaker, add 40 ml 0.1 N HCl solution and stirred with a magnetic bar at 150 rpm. Under stirring, add 25 ml of Solution 1. Mix the content for 120 seconds at 150 rpm, followed by adding 290 ml of Solution 2. Continue mixing for 15 minutes.

Pour the content of the container onto a 30 mesh screen. The insoluble hydrogel matrix structure is collected on the screen. The displacement volume $V_d$ is measured by using a 2000 ml volumetric cylinder filled with 400 ml of water ($V_0$). The screened insoluble hydrogel matrix structure is added into the volumetric cylinder and the increased volume is recorded ($V_{in}$). The $V_d$ is calculated by subtracting $V_0$ from $V_{in}$. The Hydrogel Yield Ratio (HYR, %) is calculated using the obtained $V_d$ using Equation 1. Repeat the experiment in triplicates.

| Sample ID | 8069-36C |
| --- | --- |
| Volume of 0.1N HCl Solution, mL | 40 |
| Volume of Solution 1 ($V_{Soln\ 1}$), mL | 25 |
| Volume of Solution 2 ($V_{Soln\ 2}$), mL | 290 |
| ($V_{Soln\ 1} + V_{Soln\ 2}$), mL | 315 |
| Sequence of Solution Addition | Solution 1 followed by Solution 2 |
| $V_d$, mL | 250 |
| Hydrogel Yield Ratio (HYR), % | 79.4 |

The HYR % of gel mass produced by solution addition order of Solution 1 followed by Solution 2 is much higher than that produced by solution addition order of Solution 2 followed by Solution 1.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A method for or treatment of obesity or overweight, comprising a step-wise administration of a two-portion solution system to a subject suffering from obesity or overweight, wherein the two-portion solution system comprises a first solution and a second solution and the step-wise administration comprises:
(i) administrating a unit dosage of the first solution comprising a cross-linker for crosslinking a hydrogel; and
(ii) administrating a unit dosage of the second solution comprising a cross-linkable hydrogel polymer after the administration of the first solution,
wherein the two-portion solution system forms a cross-linked hydrogel mass that is water-insoluble and has a volume of equal to or greater than 50% (v/v) of the total volume of the two-portion solution system.

2. The method of claim 1 wherein the two-portion solution system is administered no more than 2 hours prior to the subject taking a meal.

3. The method of claim 1, wherein the two-portion solution system is administered at least 10 minutes prior to the subject taking a meal.

4. The method of claim 1, wherein the two-portion solution system is administered by ingestion.

5. The method of claim 1, wherein the second solution is ingested within 1 minute after the ingestion of the first solution.

6. The method of claim 1, wherein the first solution or the second solution is provided as a beverage.

7. The method of claim 1, wherein the first solution or the second solution is used as an additive to articles of food.

8. The method of claim 1, wherein the cross-linker is provided for cross-linking an alginate, partially methoxylated pectin, or pectinate natural polymer.

9. The method of claim 1, wherein the cross-linker is a divalent salt.

10. The method of claim 9, wherein the divalent salt is a calcium salt.

11. The method of claim 10, wherein the calcium salt is selected from the group consisting of calcium phosphate, calcium carbonate, calcium sulfate, calcium oxide, calcium citrate, calcium lactate, calcium chloride, calcium ascorbate, calcium tartrate, calcium acetate, calcium gluconate, calcium propionate, calcium malate, and a combination thereof.

12. The method of claim 1, wherein the first solution is a calcium salt solution.

13. The method of claim 12, wherein the first solution has a concentration ranging from about 0.1% to about 40% (w/v).

14. The method of claim 12, wherein the first solution has a concentration ranging from about 1% to about 25% (w/v).

15. The method of claim 12, wherein the first solution has a concentration ranging from about 2% to about 22% (w/v).

16. The method of claim 1, wherein the unit dosage of the first solution has a volume of 100 mL or below.

17. The method of claim 1, wherein the cross-linkable hydrogel polymer comprises one or more natural polymers.

18. The method of claim 1, wherein the natural polymer is a polysaccharide or a salt thereof.

19. The method of claim 18, wherein the natural polymer is an alginate salt, partially methoxylated pectin, or pectin salt.

20. The method of claim 19, wherein the alginate has a molecular weight of 400,000 daltons or below.

21. The method of claim 19, wherein the alginate has a ratio of beta-D mannuronic acid to alpha-L guluronic acid equal to or below 1.

22. The method of claim 19, wherein the alginate has a ratio of beta-D mannuronic acid to alpha-L guluronic acid above 1.

23. The method of claim 19, wherein the alginate is substantially free of taste or odor.

24. The method of claim 19, wherein the pectin is a partially methoxylated pectin or a monovalent salt form thereof.

25. The method of claim 19, wherein the partial methoxylated pectin or a monovalent salt thereof comprises a LM-pectin, a HM-pectin or a combination thereof.

26. The method of claim 19, wherein the partially methoxylated pectin or monovalent pectin salt has a molecular weight ranging between about 60,000 daltons and about 130,000 daltons.

27. The method of claim 18, wherein the natural polymer is an alginate monovalent salt.

28. The method of claim 27, wherein the alginate monovalent salt is selected from the group consisting of sodium alginate, potassium alginate, ammonium alginate, and a combination thereof.

29. The method of claim 1, wherein the concentration of the cross-linkable hydrogel polymer in the second solution ranges from about 0.1% to about 10% (w/v).

30. The method of claim 1, wherein the cross-linkable hydrogel polymer in the second solution has a viscosity of between about 3.5 cps and about 450 cps as measured in a 1% (w/v) solution.

31. The method of claim 1, wherein the unit dosage of the second solution has a volume of between about 100 mL and about 1000 mL.

32. The method of claim 1, wherein the ratio of the volume of the first solution to the volume of the second solution ranges from about 3:1 to about 1:100.

33. The method of claim 1, wherein the first solution or the second solution further comprises an additive.

34. The method of claim 33, wherein the additive comprises a mono- or disaccharide.

35. The method of claim 34, wherein the mono- or disaccharide is selected from the group consisting of saccharose, glucose, invert sugar, and a mixture thereof.

36. The method of claim 33, wherein the additive comprises an artificial sweetener.

37. The method of claim 36, wherein the artificial sweetener is selected from the group consisting of Acesulfame potassium, Aspartame, Cyclamate, Mogrosides, Saccharin, Stevia, Sucralose, Sugar alcohols, and a mixture thereof.

38. The method of claim 33, wherein the additive comprises a flavoring agent.

39. The method of claim 38, wherein the flavoring agent is selected from natural flavoring agents derived from a spice, fruit or fruit juice, vegetable or vegetable juice, edible yeast, herb, bark, bud, root, leaf or similar plant material, meat, seafood, poultry, eggs, dairy products, or fermentation products thereof; or artificial flavoring agents approved by the FDA for human consumption, and a mixture thereof.

40. The method of claim 33, wherein the additive comprises a colorant.

41. The method of claim 40, wherein the colorant is a color additive approved by the FDA for use in human food and drugs.

42. The method of claim 33, wherein the additive comprises a pH adjusting agent.

43. The method of claim 42, wherein the pH adjusting agent is an organic or inorganic acid or an organic or inorganic base.

44. The method of claim 33, wherein the additive comprises a preservative.

45. The method of claim 44, wherein the preservative is selected from the group consisting of benzoic acid, benzoates, parabens, sulfur dioxide, sulfites, ascorbic acid, sodium ascorbate, gallic acid, sodium gallate, butylated hydroxytoluene (BHT), butylated hydroxyanisole (BHA), and tocopherols (Vitamin E), and a mixture thereof.

46. The method of claim 33, wherein the additive is selected from the group consisting of a protein, a lipid, a carbohydrate, a vitamin, and a mineral component.

47. The method of claim 1, further comprising administering to the subject a second agent.

48. The method of claim 1, wherein the two solution system is provided as a kit and wherein the unit dosage of the first solution and the unit dosage of the second solution are provided in separate containers.

* * * * *